(12) United States Patent
Chrysostom

(10) Patent No.: US 12,409,020 B2
(45) Date of Patent: Sep. 9, 2025

(54) THERAPEUTIC COVERING FOR HORSES

(71) Applicant: NAAR BOVEN CORPORATION, Wilmington, DE (US)

(72) Inventor: Katherine L. Chrysostom, Ocala, FL (US)

( * ) Notice: Subject to any disclaimer, the term of this patent is extended or adjusted under 35 U.S.C. 154(b) by 917 days.

(21) Appl. No.: 17/455,160

(22) Filed: Nov. 16, 2021

(65) Prior Publication Data

US 2022/0071751 A1    Mar. 10, 2022

Related U.S. Application Data

(63) Continuation-in-part of application No. 16/897,948, filed on Jun. 10, 2020, now abandoned, which is a continuation of application No. 15/221,244, filed on Jul. 27, 2016, now abandoned.

(60) Provisional application No. 62/211,305, filed on Aug. 28, 2015.

(51) Int. Cl.

| | |
|---|---|
| *A61D 9/00* | (2006.01) |
| *A01K 13/00* | (2006.01) |
| *A61F 7/00* | (2006.01) |
| *A61F 7/02* | (2006.01) |
| *A61F 7/03* | (2006.01) |
| *A61N 2/06* | (2006.01) |
| *A61N 5/06* | (2006.01) |

(52) U.S. Cl.
CPC .............. *A61D 9/00* (2013.01); *A01K 13/008* (2013.01); *A61F 7/0097* (2013.01); *A61N 2/06* (2013.01)

(58) Field of Classification Search
CPC ....... A61D 9/00; A01K 13/008; A61F 7/0097; A61F 2007/0266; A61F 7/03; A61N 2/06; A61N 2005/0645; A61N 2005/066
See application file for complete search history.

(56) References Cited

U.S. PATENT DOCUMENTS

| | | | |
|---|---|---|---|
| 4,587,956 | A | 5/1986 | Griffin et al. |
| 4,825,877 | A | 5/1989 | Kempe |
| 5,389,061 | A | 2/1995 | Nor |
| 5,426,925 | A * | 6/1995 | Smargiassi ........... A01K 13/008 |
| | | | 54/66 |
| 5,888,185 | A | 3/1999 | Regan |
| 5,984,855 | A | 11/1999 | DiNapoli |
| D419,270 | S | 1/2000 | Ruscitti |
| 6,062,008 | A | 5/2000 | Nor |
| 6,139,486 | A | 10/2000 | Matuszewski et al. |
| 6,174,277 | B1 | 1/2001 | Nichols |
| 6,652,446 | B1 * | 11/2003 | Bove ........................ A61N 2/06 |
| | | | 600/15 |

(Continued)

OTHER PUBLICATIONS

Schneiders. https://www.sstack.com/product/dura-tech-magnetic-sheet/ (Year: 2010).*

(Continued)

*Primary Examiner* — Carrie R Dorna
*Assistant Examiner* — Joshua Daryl D Lannu
(74) *Attorney, Agent, or Firm* — Douglas Wm. Massinger, ESQ.

(57) ABSTRACT

A therapeutic covering for a horse having a mesh material that is infused with ceramic mineral powder (emitting far-infrared wavelengths) and magnets coupled to the mesh material. The mesh material can have a mesh size that provides therapeutic effect, is breathable, and is bug resistant.

20 Claims, 3 Drawing Sheets

(56) References Cited

U.S. PATENT DOCUMENTS

| | | | |
|---|---|---|---|
| 6,820,574 | B2 | 11/2004 | Sharpe |
| 8,137,259 | B1 | 3/2012 | Dennis et al. |
| 8,308,627 | B2 | 11/2012 | Friberg |
| 8,376,925 | B1 | 2/2013 | Dennis et al. |
| 2004/0103622 | A1 | 6/2004 | Nor |
| 2004/0247528 | A1 | 12/2004 | Schoneberg |
| 2005/0101828 | A1 | 5/2005 | Butler et al. |
| 2005/0126134 | A1 | 6/2005 | Hathcock |
| 2006/0042199 | A1 | 3/2006 | Donahue |
| 2006/0042200 | A1 | 3/2006 | Kwan |
| 2006/0052658 | A1 | 3/2006 | Ozpapu |
| 2006/0111606 | A1 | 5/2006 | Yee |
| 2008/0216454 | A1 | 9/2008 | Lacow et al. |
| 2009/0181206 | A1 | 7/2009 | Chang |
| 2010/0056845 | A1 | 3/2010 | Hunter |
| 2010/0146914 | A1 | 6/2010 | MacDonald |
| 2011/0185688 | A1 | 8/2011 | MacGuinness |
| 2014/0257155 | A1 | 9/2014 | Altinok et al. |
| 2014/0288383 | A1 | 9/2014 | Barnett |
| 2015/0335742 | A1 | 11/2015 | Vissman et al. |
| 2016/0330934 | A1 | 11/2016 | Lundgren |

OTHER PUBLICATIONS

Chrysostom. Ceramic Fabric Therapy for Horses, Jul. 22, 2014 (Year: 2014).*

Schneiders. NPL 15221244DuraTechMangeticSheetMarch_6_201 O (attached), Mar. 6, 2010, Dura Tech (https://web.archive.org/web/20100306155850/https://www.sstack.com/product/dura-tech-magnetic-sheet) (Included in Notice of References Cited dated Apr. 6, 2018 for U.S. Appl. No. 15/221,244).

Hamblin et. al. Far infrared radiation (FIR): its biological effects and medical applications.Photonics Lasers Med. Nov. 1, 2012; 4: 255-266 (Included in Notice of References Cited dated Apr. 6, 2018 for U.S. Appl. No. 15/221,244).

Kat Chrysostom. Ceramic Fabric Therapy for Horses. Published Jul. 22, 2014. (Included in Notice of References Cited dated Apr. 6, 2018 for U.S. Appl. No. 15/221,244).

DePaolo; Therapeutic treatments for horses; May 28, 2014; DePaolo Equine Concepts Blog. https://depaoloequineconcepts.wordpress.com/2014/05/28/therapeutic-treatments-for-horses/ (Included in Notice of References Cited dated Jan. 10, 2020 for U.S. Appl. No. 15/221,244).

English Translation of CN 1302671 A. Attached as N PL_CN 1302671A_EngTranslation_July11_2001. (Included in Notice of References Cited dated Jan. 10, 2020 for U.S. Appl. No. 15/221,244).

Declaration of Katherine Chrysostom Under 37 C.F.R Section 1.132, filed on Nov. 7, 2019 for U.S. Appl. No. 15/221,244, filed Jun. 1, 2021 for U.S. Appl. No. 16/897,948.

Second Declaration of Katherine Chrysostom Under 37 C.F.R Section 1.132, filed on Jun. 10, 2020 for U.S. Appl. No. 15/221,244, filed Jun. 1, 2021 for U.S. Appl. No. 16/897,948.

Third Declaration of Katherine Chrysostom Under 37 C.F.R Section 1.132, filed on Jun. 1, 2021 for U.S. Appl. No. 16/897,948.

M.A. Gunkelman, B.J. Karren, J.A. Altman, C.J. Hammer, Effects of a magnetic/ceramic therapy sheet on horses with back pain, Journal of Equine Veterinary Science, May 2017, pp. 97-98, vol. 52, Elsevier Inc., United States.

USEF Guidelines & Rules for Drugs and Medications, last revised Jul. 2020, pp. 1-22, United States Equestrian Federation, United States.

* cited by examiner

THERAPEUTIC COVERING FOR HORSES

CROSS-REFERENCE TO RELATED APPLICATIONS

This application is a continuation-in-part of U.S. Non-provisional patent application Ser. No. 16/897,948, filed Jun. 10, 2020, which is a continuation of U.S. Non-provisional patent application Ser. No. 15/221,244 filed on Jul. 27, 2016, which claims the benefit of U.S. Provisional Patent Application No. 62/211,305 filed Aug. 28, 2015, the contents of which applications are herein incorporated by reference in their entirety.

COPYRIGHT NOTICE

A portion of the disclosure of this patent document may contain material which is subject to copyright protection. The copyright owner has no objection to the facsimile reproduction by anyone of the patent document or the patent disclosure, as it appears in the Patent and Trademark Office patent file, but otherwise reserves all copyright rights whatsoever. 37 FR 1.71(d).

FIELD OF THE DISCLOSURE

The present disclosure generally relates to the field of magnetic and ceramic textile therapies, and more specifically relates to a therapeutic covering for equine use.

BACKGROUND

Competition horses are tested for illegal substances before competitions. In some competitions, there is a 12-hour administration rule for any medication prior to competition. Training can cause soreness in a horse, and the horse may need help with discomfort associated with training and even injuries resulting from competition and training. For example, for back soreness of a horse, the most commonly prescribed medication for soreness relief is methocarbamol, which is a muscle relaxant. The maximum dosage of methocarbamol currently allowed is 5.0 g/1000 lbs, and methocarbamol is administered orally or intravenously at least 12 hours prior to competition. There are also restrictions on NSAIDS and natural anti-inflammatory drugs prior to competition for horses.

There is a need for an effective, non-invasive, non-medicinal, and non-detectable technique for treating horse soreness and discomfort.

SUMMARY

Disclosed is a therapeutic covering for a horse comprising a mesh material infused with a ceramic mineral powder, and a plurality of magnets coupled to an outer surface of the mesh material, wherein the mesh material has a mesh size in a range of greater than 2.5 millimeters and less than about 5 millimeters.

Also disclosed herein is a method for ceramic and magnetic therapy on a horse. The method can include placing the therapeutic covering on a horse; and allowing the therapeutic covering to perform ceramic and magnetic therapy on the horse. The therapeutic covering can be of any embodiment disclosed herein. The method can further include positioning the therapeutic covering on the horse such that the magnets are positioned to correspond with acupuncture points of the horse.

BRIEF DESCRIPTION OF THE DRAWINGS

The figures which accompany the written portion of this specification illustrate embodiments and method(s) of use for the therapeutic covering.

The various embodiments of the disclosure will hereinafter be described in conjunction with the appended drawings.

DETAILED DESCRIPTION

Disclosed herein is a therapeutic covering for horses that is made of a mesh material infused with ceramic mineral powder. The therapeutic covering also has magnets that are coupled to the mesh material in positions that correspond with the primary acupuncture points of the horse or pony when the therapeutic covering is placed over the horse or pony. The therapeutic covering provides a combination therapeutic effect, is breathable, and is unexpectedly bug resistant.

The ceramic particles in the ceramic mineral powder provide ceramic therapy. The ceramic particles emit far-infrared wavelengths which stimulate vibration of the oxygen atoms within the water molecules ($H_2O$). As the oxygen atom in each water molecule vibrates around the hydrogen atoms, the water molecules begin to shrink in size which then stimulates the increase in blood circulation as well as dilation of blood vessels. Ceramic therapy can also help develop new capillaries (branching blood vessels with a hair-like thickness) for treatment of deep muscle lesions or soft tissue injuries.

The magnets provide magnetic therapy. Magnetic therapy is an accepted alternative medicine practice that involves the use of static or pulsing magnetic fields to derive beneficial health effects such as oxygenating soft tissues, stimulating blood flow in underlying tissues, improving overall immunity, and creating the harmonization of bodily functions.

The combination of ceramic therapy and magnetic therapy provided by the disclosed therapeutic covering offers a unique, safe, and non-invasive treatment for horses. The therapeutic benefits of this combination therapy can be used as pre-exercise and/or post-exercise therapy for horses. For example, the therapeutic covering can help to "warm-up" or stimulate a horse's muscles and relax tension before exercise. Additionally or alternatively, the therapeutic covering can help to reduce soreness, reduce inflammation, and increase blood circulation for enhanced healing and recovery as a post-exercise therapy.

Figure 1:
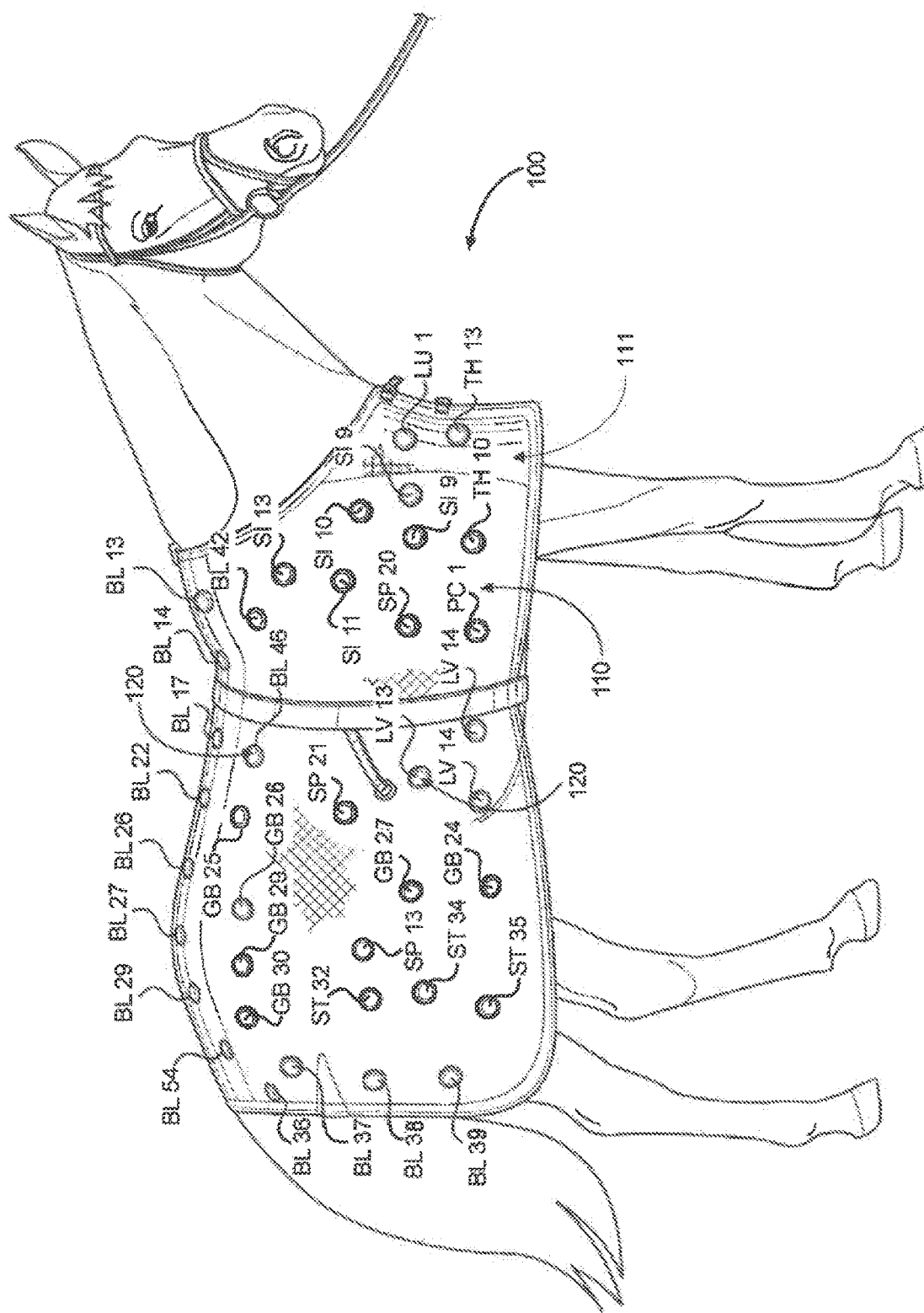
FIG. 1 is a side view illustrating a therapeutic covering on a horse according to the disclosure.
Figure 2:
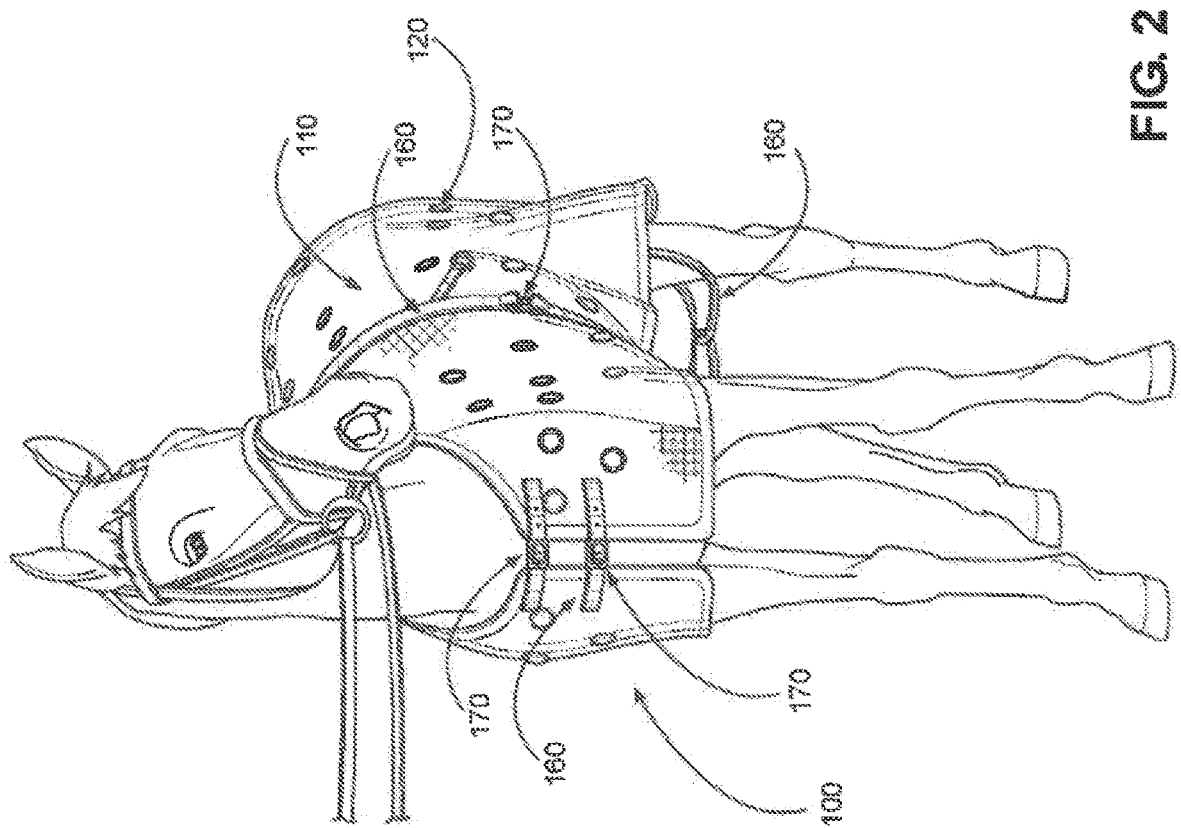
FIG. 2 is a perspective view of the therapeutic covering and horse of FIG. 1.
Figure 3:
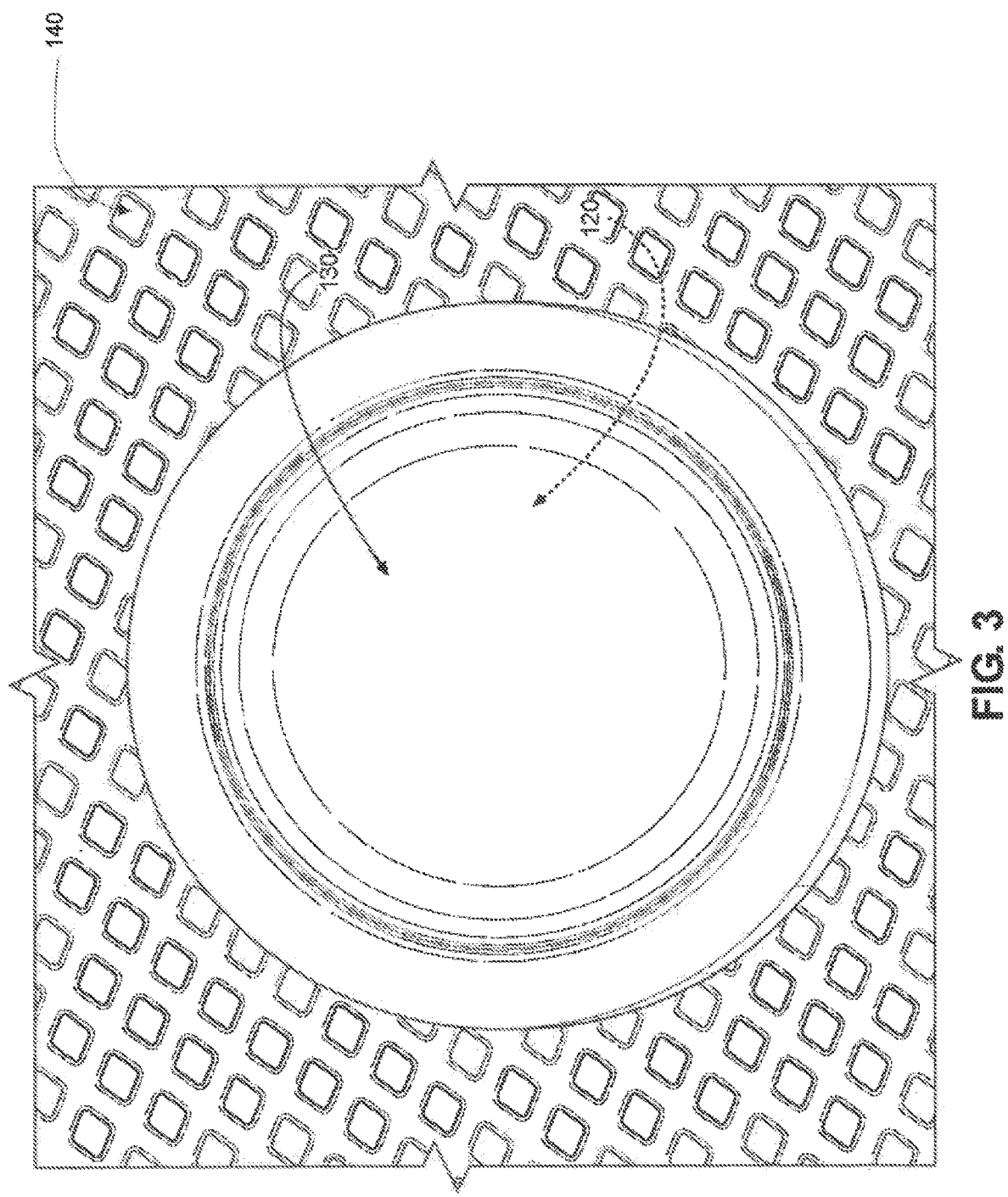
FIG. 3 is an isolated plan view illustrating a pocket of the therapeutic covering having a magnet therein.

Referring now to FIGS. 1-3, the therapeutic covering 100 is shown placed on a horse. The therapeutic covering 100 has a mesh material 110 configured to cover at least a portion of a horse's body. The mesh material 110 is infused with ceramic mineral powder, and a plurality of magnets 120 are attached to an outer surface 111 of said mesh material 110 at predetermined locations. In embodiments, the predetermined locations can correspond to acupuncture points of the horse when the therapeutic covering 100 is placed on the horse.

The mesh material 110 can be made of moisture wicking fibers that can include, but are not limited to, polyester, polypropylene, nylon, micro modal, bamboo, wool, or combinations thereof. The moisture wicking and fibers can pull moisture away from the horse's skin to help keep the horse cooler, to help the horse dry faster after being wet, or both. Moreover, the moisture wicking fibers can be chosen for the suitability to infuse ceramic powder into the fibers.

In embodiments, the mesh material 110 can be a net of knitted strands of fibers. For example, the mesh material 110 can have a warp-knitted structure. In embodiments, the warp-knitted structure can be a 20-needle warp-knitted structure.

In embodiments, the mesh material 110 can be a heavyweight mesh or heavyweight net. "Heavyweight" is defined as weighing more than 50 g/m (45.87 g/yd). A heavyweight mesh or net can be used to provide a light covering for the horse that can fit under or over other blankets or equipment while also being heavy enough to follow the contour of the horse while the therapeutic covering 100 is in use. In embodiments, the mesh material 110 can weigh 295 g/m (270 g/yd). The mesh material 110 can also be durable such that the mesh material 110 is hard to tear with normal usage. The mesh material 110 can have a high tensile strength allowing the covering to be pulled and grabbed during use without tearing or breaking. The mesh material 110 can have a tensile strength in the warp direction in a range of about 9.84 kg/cm (25 kg/in) to about 13.77 kg/cm (35 kg/in); alternatively, about 10.62 (27 kg/in) to about 12.6 kg/cm (32 kg/in); alternatively, a tensile strength of about 11.41 kg/cm (29 kg/in) in the warp direction. The mesh material 110 can have a tensile strength in the weft direction in a range of about 7.87 kg/cm (20 kg/in) to about 11.81 kg/cm (30 kg/in); alternatively, about 9.06 kg/cm (23 kg/in) to about 10.62 kg/cm (27 kg/in); alternatively, a tensile strength of about 9.84 kg/cm (25 kg/in) in the weft direction.

The mesh material 110 is characterized by having openings (e.g., see opening 140 in FIG. 3) between fibers or strands of fibers. The openings can have any shape, such as but not limited to circle shape, oval shape, triangle shape, square shape, rectangle shape, diamond shape, or combinations thereof. The mesh size of the mesh material 110 is defined by the size of the openings (e.g., see opening 140 in FIG. 3) in the mesh material 110. The openings in the mesh material 110 is large enough to be breathable. "Breathable" as used herein means the openings in the mesh material are of a size that allows horse body heat to transfer through the openings of the therapeutic covering and for ambient air to transfer through the same openings. It was found that a mesh size of 2.5 millimeters or less (e.g., the mesh size of the mesh material of a typical scrim) was too small to be breathable for a horse in a warm or hot climate that does not need to keep warm. That is, a mesh size of 2.5 millimeters or smaller led to sweating of horses when not desired. In the therapeutic covering 100 disclosed herein, the mesh size (e.g., the largest distance of opening 140) of the mesh material 110 can be greater than 2.5 millimeters to about 5 millimeters; alternatively, greater than 2.5 millimeters to about 4 millimeters; alternatively, from about 3 millimeters to about 4 millimeters; alternatively, a width of about 3.5 millimeters; alternatively, a width of 3.5 millimeters. The "largest distance" of an opening depends on the shape of the opening. For example, the largest distance of a circle shaped opening is the diameter of the circle, the largest distance of an oval-shaped opening is the major diameter, the largest distance of a triangle-shaped opening is the longest side of the triangle, the longest distance of a square-shaped opening is any side of the square, the largest distance of a rectangular shaped opening is the longest side, the largest distance of a diamond shaped opening is the major axis.

It was surprisingly found that a mesh size in the disclosed range was not only breathable, the mesh size visually reduced horse irritation from bugs (e.g., flies). The bugs unexpectedly leave the horse to pursue other horses not wearing the therapeutic covering 100. While not being limited by theory, it is believed that the flies are deterred from targeting the horse even though the mesh size is large enough for the flies to touch the horse's fur and/or skin. While small (2.5 millimeters or less) mesh sizes can physically prevent insects and bugs from landing on the skin of the horse because the openings are smaller than insect size in some cases, it was unexpected and surprising that a mesh size of greater than 2.5 millimeters to about 5 millimeters led to the insects leaving the horse alone rather than continuing to try and land on the horse in the openings 140 of the mesh material 110.

The mesh material 110 can also be infused with a ceramic mineral powder. More particularly, the fibers of the mesh material 110 can be infused with the ceramic mineral powder. The ceramic mineral powder may be formed as a combination of lead-free materials including, but not being limited to, silica, magnesia, alumina, copper, titania, zirconia, silicon carbide, mullite, rare earth phosphates, or combinations thereof. The ceramic particles that make up the powder can be infused via any technique known in the art with the aid of this disclosure. For example, the ceramic particles can be infused by incorporating the ceramic particles into the polymers strands that make up the fabric. Additionally or alternatively, the ceramic particles can be melted into a slurry that is then contacted with the fibers of the mesh material so that the ceramic particles absorb into the fibers. Additionally or alternatively, the ceramic particles can be added to a solve to make a solution, the fabric is then placed in the solution, and then current is applied to the solution having the fibers placed therein to bond the ceramic particles to the fibers. Different methods can be chosen based on the type of fibers used for the mesh material 110 and the particular species of ceramic particles used. Infusion conditions such as concentration of ceramic particles in the slurry or solution, solution temperature, slurry temperature, the pH of the solution, the pH of the slurry, contact time of the fibers with the solution or slurry, and amount of current applied to the solution can be chosen based on the type of fibers and species of ceramic particles.

Fabric that is infused with a ceramic mineral powder can offer therapeutic benefits to horses. The types of ceramic mineral powders can create thermally induced photoluminescence emitting light with a wavelength in the "far-infrared" region of the electromagnetic spectrum. Simple body heat is enough thermal energy to induce the infused ceramic powder in the fabric to emit the "far-infrared" light. Infrared light, as well as far-infrared light, has shown the ability to help cells regenerate and repair themselves as well as improve circulation of oxygen-rich blood through the body. Oxygen-rich blood is often needed in areas of the body experiencing pain and deep tissue injuries. By helping improve the flow of oxygen-rich blood, infrared light can promote faster healing and pain relief. Infrared light has also been shown to help reduce inflammation. Infrared light is produced by the sun but is not harmful, in contrast to ultraviolet light. The infrared light is absorbed by photoreceptors in cells, which can then trigger numerous natural processes of the cells offering the aforementioned benefits. Infrared light therapy has been applied to treating back pain, arthritis, bursitis, muscle strain, neck pain, tendonitis, blunt trauma, and more in humans.

Research has shown that infrared light therapy can be just as beneficial for horses as humans. Infrared light used in therapy for humans penetrates about 2 to 7 centimeters under the skin to reach muscles. While this can work on humans, horses have many areas where deep tissue is deeper than 7 centimeters. Far-infrared light has been shown to penetrate deeper than 7 centimeters making far-infrared light the ideal choice for use in horses. Embodiments of the therapeutic covering 100 can have a far-infrared emissivity wavelength equal to or greater than 8 micrometers. A far-infrared emissivity wavelength in the range of 8 to 14 micrometers has been proven to be most beneficial for health, and embodiments disclosed of the mesh material 110 disclosed herein can have a far-infrared emissivity wavelength in the range of from about 8 to about 14 micrometers. It has been shown that humans, and certain animals including horses, feel far-infrared light simply as heat.

The therapeutic covering 100 made of a mesh material 110 infused with ceramic mineral powder can offer numerous therapeutic benefits to the horses. As mentioned above infrared light and far-infrared light has been shown to help promote cell repair and pain relief in the horses. When the therapeutic covering 100 is placed over the horse, the body heat of the horse can activate the ceramic minerals infused into the mesh material 110. When activated, the ceramic minerals begin emitting far-infrared light that can gently heat the horse's muscles and promote blood flow throughout the body.

In embodiments, the therapeutic covering 100 can include a plurality of attachment members 160. Each of the attachment members 160 can be connected to the mesh material 110 and can be adapted to connect spaced portions of the mesh material 110 such that the mesh material 110 can be secured in place upon the horse's body. The plurality of attachment members 160 can be formed as adjustable strap members having releasable connectors 170 attached thereto. The plurality of attachment members 160 can be made of polyester, nylon, acrylic, cotton, or combinations thereof. The plurality of attachment members 160 can be designed to secure two ends of the therapeutic covering 100 together, as seen with the front of the therapeutic covering 100 in FIG. 2; alternatively, the plurality of attachment members 160 can be designed to encircle the horse and secure the two ends together, but also secure the therapeutic covering 100 to the horse as depicted in FIGS. 1 and 2. The releasable connectors 170 can be buckles, clasps, ties, hook and loop, or other securing mechanisms. The releasable connectors 170 can be made of plastic, metal, wood, fabric, or combinations thereof.

In addition to being infused with ceramic minerals, the therapeutic covering 100 can also have magnets 120 coupled to the mesh material 110. The locations of the magnets 120 can correspond to acupuncture points of the horse when the therapeutic covering 100 is placed on the horse, to offer further therapeutic benefits and combination therapy to the horse. The magnets 120 can be coupled to the mesh material 110 by attachment, such as by sewing, glue, hook and loop, clips, or combinations thereof. Alternatively, the magnets 120 can be placed in pockets formed on the therapeutic covering 100, as is described for FIG. 3 below.

FIG. 3 is an isolated plan view illustrating a pocket 130 of the therapeutic covering 100 having a magnet 120 placed therein. While one pocket 130 is illustrated for one magnet 120 in FIG. 3, it is contemplated that any number of pocket and magnet pairs can be utilized with the therapeutic covering 100. The pocket 130 can be of a size just large enough to accept one of the magnets 120, so that the magnets 120 do not slide or move from the designated acupuncture point when the therapeutic covering 100 is placed over the horse. In embodiments, the fabric of the pocket 130 can be sewn to enclose the magnet 120 into the pocket 130. The pocket 130 can be made of the same material as the mesh material 110, or another suitable material. In embodiments of the therapeutic covering 100, the magnets 120 can be removeable. In additional or alternative embodiments, the therapeutic covering 100 can have multiple sets of magnets 120 of different strengths that may be placed on the therapeutic covering 100 based on the needs of the horse at the time.

In embodiments, each of the magnets 120 can be neodymium magnets. Neodymium magnets are made from an alloy of neodymium, iron, and boron. Neodymium magnets are the strongest type of permanent magnet that is available commercially. Alternatively, other rare-earth magnets can be used for any of the magnets 120. Other rare-earth metal magnets may be used to achieve specific strengths or to control a manufacturing cost of the therapeutic covering 100.

In embodiments, the therapeutic covering 100 can have about 80 to about 150 magnets 120. Alternatively, more magnets 120 can be used in embodiments of the therapeutic covering 100. Other embodiments of the therapeutic covering 100 can have fewer magnets 120 to reduce the cost, weight, or provide magnet therapy to the acupuncture points on only specific regions of the horse. The number of magnets 120 used on a given therapeutic covering 100 can depend on the size of the therapeutic covering 100 and the size of the horse or pony for which the therapeutic covering 100 is designed.

In embodiments, one or more of the magnets 120 can have a strength in a range of about 1100 to about 2400 Gauss. In other embodiments, one or more of magnets 120 can have a strength lower than 1100 Gauss for smaller horses and ponies or if the targeted problem is closer to the surface and weaker magnets can suffice. Other embodiments can also have magnets with a strength higher than 2400 Gauss. Magnets with a strength as high as 5000 Gauss can be used safely for therapy, and embodiments of the therapeutic covering 100 can utilize magnets with a strength of up to 5000 Gauss. Magnets used in therapy for humans often are in a range of 300 to 500 Gauss.

The magnets 120 are placed over the primary acupuncture points including, but not limited to: release points that line the vertebrae, ulcer-prone areas and stomach, shoulders, haunches, and rib cages. FIG. 1 shows the plurality of magnets 120 can be placed on acupuncture points including Bladder channel points: BL 13, BL 14, BL 17, BL 22, BL 26, BL 27, BL 29, BL 54, BL 36, BL 37, BL 38, BL 39, BL 42, BL 46; Gall Bladder channel points: GB 24, GB 25, GB 26, GB 27, GB 29, GB 30; Small Intestine channel points: SI 13; SI 10, SI, 11, SI 9; Spleen channel points: SP 21, SP 13, SP 20; Lung channel points: LU 1; Stomach channel points: ST 32, ST 34, ST 35; Liver channel points: LV 13, LV 14; Pericardium channel points: PC 1; and Triple Heater channel points: TH 10, TH 13. The magnets 120 can also be placed on the side of the therapeutic covering 100 not depicted in FIG. 1 over similar acupuncture points as those depicted. The therapeutic covering 100 is cost-effective to produce in the embodiments.

The therapeutic covering 100 uses a combination of the ceramic mineral powder infused in the mesh material 110 and the attached magnets 120 to offer combination therapy to horses in a non-invasive manner. Competition horses are tested for certain substances that violate the competition rules (steroids or similar performance enhancing drugs)

during said competitions. Medication designed to aid the competition horses with things such as back-soreness relief and reducing inflammation can be detected in these tests. If detected, the horse can be expelled from the competition. The therapeutic covering 100 offers an alternative to these drugs that cannot be detected in the blood or urine tests by offering relief through combination therapy that does not involve administering substances that enter the horse's bloodstream. Embodiments of the therapeutic covering 100 can have extensions to fit over a horse's tack so that the therapeutic covering 100 can be left on the horse, offering therapy and relief, until the rider mounts the horse. As the therapeutic covering 100 offers breathability and insect resistance, the therapeutic covering 100 is also able to be worn and offer relief to the horse during transport to the competition.

Also disclosed herein is a method for ceramic and magnetic therapy of a horse. The method can include placing the therapeutic covering 100 on a horse; and allowing the therapeutic covering 100 to perform ceramic and magnetic therapy on the horse. The therapeutic covering 100 can be of any embodiment disclosed hereinabove. The method can further include positioning the therapeutic covering 100 on the horse such that the magnets 120 are positioned to correspond with acupuncture points of the horse. The method achieves the unexpected and surprising results disclosed above via use of the therapeutic covering 100 for the ceramic and magnetic therapy of the horse.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. A therapeutic covering for a horse, the therapeutic covering comprising:
   a mesh material infused with a ceramic mineral powder and configured to cover at least a portion of the horse, wherein the mesh material has a mesh size in a range of greater than 2.5 millimeters and less than 5 millimeters; and
   a plurality of magnets coupled to an outer surface of the mesh material.

2. The therapeutic covering of claim 1, wherein the mesh size is in a range of from 3 millimeters to 4 millimeters.

3. The therapeutic covering of claim 2, wherein the mesh size is 3.5 millimeters.

4. The therapeutic covering of claim 1, wherein the mesh material is a net of knitted strands of fibers.

5. The therapeutic covering of claim 4, wherein the fibers are made of polyester, polypropylene, nylon, micro modal, bamboo, wool, or combinations thereof.

6. The therapeutic covering of claim 4, wherein the net comprises a warp-knitted net.

7. The therapeutic covering of claim 1, wherein each of the plurality of magnets is a neodymium magnet having a strength in a range of 1100 to 2400 Gauss.

8. The therapeutic covering of claim 7, wherein the plurality of magnets comprises from 80 to 150 magnets.

9. The therapeutic covering of claim 1, wherein the plurality of magnets are positioned on the outer surface of the mesh material to correspond with acupuncture points of the horse when the therapeutic covering is placed on the horse.

10. The therapeutic covering of claim 1, further comprising a plurality of pockets formed on the outer surface of the mesh material, wherein each of the plurality of pockets is configured to receive and hold one of the plurality of magnets.

11. The therapeutic covering of claim 1, wherein the ceramic mineral powder is made of silica, alumina, magnesia, or a combination thereof.

12. The therapeutic covering of claim 1, wherein the ceramic mineral powder is configured to emit far-infrared light at a wavelength of greater than 8 micrometers when the therapeutic covering is placed on the horse.

13. The therapeutic covering of claim 1, further comprising:
   a plurality of attachment members coupled to the mesh material, the attachment members having a corresponding number of releasable connecters.

14. The therapeutic covering of claim 1, wherein the mesh material is a net of knitted strands of fibers.

15. The method of claim 14, wherein the fibers are made of polyester, polypropylene, nylon, micro modal, bamboo, wool, or combinations thereof.

16. The method of claim 14, wherein the ceramic mineral powder is made of silica, alumina, magnesia, or a combination thereof; and wherein each of the plurality of magnets is a neodymium magnet.

17. A method for ceramic and magnetic therapy of a horse, the method comprising the steps of:
   placing a therapeutic covering on the horse; and
   allowing the therapeutic covering to perform ceramic therapy and magnetic therapy on the horse;
   wherein the therapeutic covering comprises i) a mesh material infused with a ceramic mineral powder and configured to cover at least a portion of a horse, wherein the mesh material has a mesh size in a range of greater than 2.5 millimeters and less than 5 millimeters, and ii) a plurality of magnets coupled to an outer surface of the mesh material.

18. The method of claim 17, wherein the mesh size is in a range of from 3 millimeters to 4 millimeters.

19. The method of claim 18, wherein the mesh size is 3.5 millimeters.

20. The method of claim 17, further comprising:
   positioning the therapeutic covering on the horse such that the plurality of magnets are positioned to correspond with acupuncture points of the horse.

* * * * *